United States Patent [19]

Floyd

[11] Patent Number: 6,080,686

[45] Date of Patent: Jun. 27, 2000

[54] SOFT CELLULOSIC NONWOVENS AND A METHOD FOR SOFTENING NONWOVENS

[75] Inventor: David Thomas Floyd, Midlothian, Va.

[73] Assignee: Th. Goldschmidt AG, Essen, Germany

[21] Appl. No.: 08/006,350

[22] Filed: Jan. 19, 1993

[51] Int. Cl.$^7$ .................................................. D21H 11/00
[52] U.S. Cl. ........................ 442/102; 442/157; 162/164.4
[58] Field of Search ...................... 524/379, 385; 525/477; 428/375; 442/102, 157; 162/164.4

[56] References Cited

U.S. PATENT DOCUMENTS

| | | | |
|---|---|---|---|
| 4,395,454 | 7/1983 | Baldwin | 428/290 |
| 4,921,895 | 5/1990 | Schaefer et al. | 524/379 |
| 4,950,545 | 8/1990 | Walter et al. | 428/446 |
| 5,059,282 | 10/1991 | Ampulski et al. | 162/111 |

OTHER PUBLICATIONS

Websters New World Dictionary, 1988 p. 226.

*Primary Examiner*—Christopher Raimund
*Attorney, Agent, or Firm*—Frommer Lawrence & Haug LLP

[57] ABSTRACT

A method for softening nonwovens suitable for sanitary or cosmetic purposes or nonwoven polyolefin based webs whereby the organosilicone compounds are applied to the nonwoven materials.

19 Claims, No Drawings

SOFT CELLULOSIC NONWOVENS AND A METHOD FOR SOFTENING NONWOVENS

FIELD OF INVENTION

The invention relates to soft nonwovens and a method for softening nonwovens suitable for sanitary or cosmetic purposes, particularly nonwovens of cellulose fibers for handkerchiefs, face towels or toilet paper, or nonwovens polyolefin based webs such as polyethylene, oxidized polyethylene, polypropylene, oxidized polypropylene or combinations thereof.

BACKGROUND INFORMATION AND PRIOR ART

Nonwoven materials are used on a large scale and come into contact with the human skin during use. An important property of this product is a soft, pleasant touch, which imparts to the user the sensation of care and of pleasant use. The products must satisfy high requirements with respect to tolerance and physiological harmlessness. In many cases, it is desired that the products impart to the skin a certain film of skin-care substances, which, in turn, has a softening and smoothing effect on the skin.

The U.S. Pat. No. 4,395,454 discloses an absorbing, bioactive, easily wettable medicinal substrate of nonwoven cellulose material, which contains a bioactive, non-leachable content of 3-(trimethoxysilyl)-propyloctadecyl-dimethylammonium chloride in an amount of 0.15 to about 1.05% by weight, based on the weight of substrate. In addition, the substrate should contain 0.25 to about 1.25% by weight of a wettable, hydrophilic coupling agent, which is an organosilicone terpolymer of the formula

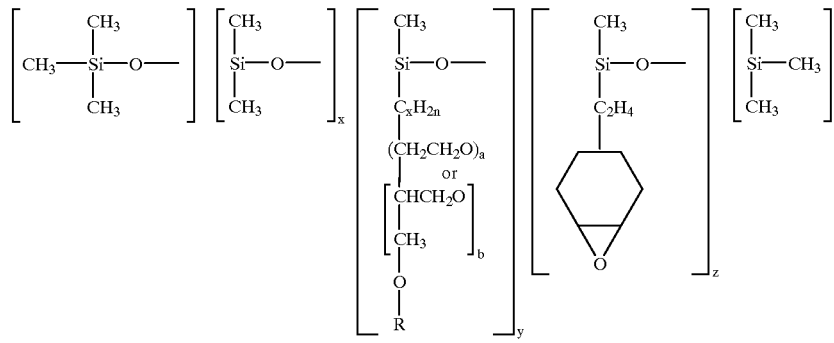

and a substantive dye in an effective amount. At the same time, the bioactive, cationic silane, the hydrophilic coupling agent and the dye are to be linked to the fibers of the cellulose substrate in such a manner, that they essentially cannot be leached out.

U.S. Pat. No. 5,059,282 discloses a tissue paper containing a silicone compound but the inventive polysiloxanes as described in the present application are neither disclosed nor can they be arrived at from this patent.

Similarly, U.S. Pat. No. 4,950,545 relates to face towels of at least two layers. These face towels contain 0.1 to about 5% by weight of a silicone with an average molecular weight of about 10,000 or more, the silicone being applied with an aqueous carrier on the layers of the face towel. The face towel, so treated, is to have a smear index of 1.0 or less, a lint reduction index of 5 or more and a sink time of not more than 30 seconds longer than that of the untreated face towel.

The smear index is a numerical measure of the smearing of a glass plate when the treated face towel is rubbed on this plate under certain conditions. The lint reduction index is a numerical measure of the decrease in lint formation during use. The sink time indicates the wettability of the treated face towel. For a more detailed description of these concepts and their measurement, reference is made to the U.S. Pat. No. 4,950,545.

In the U.S. Pat. No. 4,950,545, the following are named as silicones:

polydimethylpolysiloxanes, mixtures of these compounds with polyoxyalkylene polysiloxanes, organo-modified organo-polysiloxanes.

However, aqueous mixtures of tetraethoxysilanes, dimethyldiethoxysilanes and polyoxyalkylene polysiloxanes are also named. In this connection, the polyoxyalkylene polysiloxanes are to act as coupling agent for bonding the silanes to the fibers.

Schaeffer, U.S. Pat. No. 4,921,895, describes specific polysiloxanes suitable for finishing textile fibers and products. These products, however, are unable to fulfill all the requirements with respect to the handle and the property of having the skin appear smoother upon use of the towels.

OBJECTS OF THE INVENTION

An object of the present invention is soft nonwovens. Another object of the invention is a method for softening nonwovens suitable for sanitary or cosmetic purposes, such as handkerchiefs, face towels, toilet paper, facial tissue or for nonwoven polyolefin based webs such as polyethylene, oxidized polyethylene, polypropylene, oxidized polypropylene or combinations thereof. Another object of the invention is the inventive organosilicone compounds that, on application, render nonwovens soft.

SUMMARY OF THE INVENTION

The inventive medium to render nonwovens soft is characterized in that it contains 45 to 98% by weight of a water soluble or water dispersible polyether polysiloxane A, the polyether groups of which consist of 30 to 100 mole percent of oxyethylene units, the remainder being oxypropylene units, and the polysiloxane block of which has 10 to 100 siloxane units;

1 to 20% by weight of a water soluble or water dispersible cationic organopolysiloxane B with at least one ammonium group linked over a carbon atom;

1 to 20% by weight of a water soluble alkylene glycol;

0 to 15% by weight of a water soluble or water dispersible, nonionic surfactant;

0 to 10% by weight of a water dispersible or insoluble organopolysiloxane C;
0 to 5% by weight of a water insoluble organopolysiloxane D; and
0 to 5% by weight of a water insoluble organopolysiloxane E provided the ratio of polysiloxanes A:B is between about 12:1 and 19:1.

The inventive medium can additionally have further components such as dyes, preservatives or odor-imparting materials, which are not essential for the properties aimed for, such as an improvement in the touch.

The medium preferably is dissolved before its use in water in such an amount that the water contains 20 to 50% by weight of the medium.

The preparation can be sprayed, imprinted or printed on the nonwoven material. The amount of water, brought into the nonwoven material by the application of the medium, is of no consequence, since these nonwovens always contain a certain amount of moisture. The nonwoven materials can, of course, also be immersed in concentrated, aqueous solutions. In so doing, the medium is applied on the nonwoven material in such an amount, that the content of the medium in nonwoven material is about 0.3% by weight to 5% by weight, based on the weight of the nonwoven material.

The nonwoven material utilized in the present invention includes, among other things, materials such as handkerchiefs, face towels, toilet paper, facial tissue. It also includes nonwoven polyolefin based webs such as polyethylene, oxidized polyethylene, polypropylene, oxidized polypropylene or combinations thereof.

The water soluble or water dispersible polyether siloxane A preferably corresponds to the general, average formula

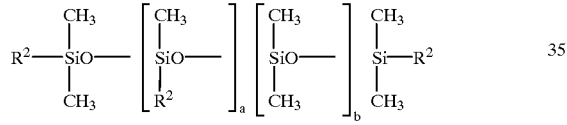

in which
$R^2$ in the molecule is the same or different and represents an alkyl group with 1 to 12 carbon atoms or a polyether group —$(C_nH_{2n}O)_xR^3$, wherein $R^3$ is a hydrogen, alkyl or acyl group and n has a numerical value of 2 to 2.7 and x has a numerical value of 2 to 200, with the proviso that at least one $R^2$ group in the average molecule must be a polyether group;
a has a numerical value of 0 to 98;
b has a numerical value of 0 to 98; and
a+b is 8 to 98.

$R^2$ can be an alkyl group with 1 to 12 carbon atoms or a polyether group. However, the condition must be fulfilled that at least one $R^2$ in the average molecule must be a polyether group. Preferably, 2 to 5 of the $R^2$ groups are polyether groups, the remaining $R^2$ groups then having the meaning of an alkyl group, the methyl group being preferred. The alkyl group can, however, have up to 12 carbon atoms. By these means, it is possible to vary the properties of the inventive medium so as to improve the handle of the nonwoven material treated with it.

The polyether groups corresponds to the formula —$(C_nH_{2n}O)_xR^3$. The subscript n has a numerical value of 2 to 2.7. In general, the polyether group consists of a plurality of oxyethylene and, optionally, oxypropylene groups. If the subscript n is 2, the polyether group consists exclusively of oxyethylene units. As the numerical value of n increases, the number of oxypropylene units present also increases. The numerical value n=2.7 means that 70 mole percent of the polyether group is an oxypropylene group.

The subscript x indicates the number of oxyalkylene units. This value is an average numerical value, since a mixture of products of different chain length usually is obtained during the synthesis of a polyether. The subscript x has a numerical value of 2 to 200 and preferably of 10 to 50. Polyether groups, which have an average molecular weight of 600 to 4,000, are preferred.

The subscript "a" indicates the number of methylsiloxy units that carry the $R^2$ group. The subscript "b" corresponds to the number of dimethylsiloxy units. While a+b can assume a value of 0 to 98, the condition must be fulfilled that the sum, a+b, has a value of 8 to 98.

If a=0, the polyether group or groups is/are linked terminally. The siloxanes with positive values for "a" are modified laterally (comb-like) by the $R^2$ groups. Siloxanes, in which the $R^2$ groups are linked laterally (comb-like), are preferred. The $R^3$ group can be a hydrogen, hydroxyl, alkyl or acyl group. Preferably, $R^3$ is a hydrogen group. If $R^3$ is an alkyl group, the lower alkyl groups with 1 to 4 carbon atoms are preferred. The acetyl group is the preferred acyl group.

Examples of suitable polyether siloxanes A are

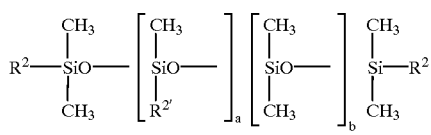

EXAMPLE 1

$R^2$=—$CH_3$ $R^{2'}$=—$(CH_2)_3$—O—$(C_2H_4O)_{17}(C_3H_6O)_2$—H a=5 b=18

EXAMPLE 2

$R^2$=—$CH_3$ $R^{2'}$=—$(CH_2)_3$—O—$(C_2H_4O)_3(C_3H_6O)_{10}$—H a=5 b=20

EXAMPLE 3

$R^2$=—$CH_3$ $R^{2'}$=—$(CH_2)_3$—O—$(C_2H_4O)_{31}(C_3H_6O)_4$—H a=5 b=75

EXAMPLE 4

$R^2$=—$(CH_2)_3$—O—$(C_2H_4O)_{16}(C_3H_6O)_{17}$—$CH_3$ $R^{2'}$=Not Applicable a=0 b=58

In the inventive medium, the siloxane B preferably is a siloxane of the general, average formula

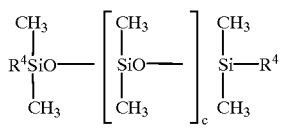

wherein $R^4$ represents the group of the formula

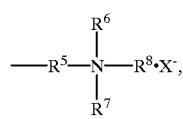

in which $R^5$ is a divalent hydrocarbon group, the carbon chain of which may be interrupted by an oxygen atom, $R^6$, $R^7$, $R^8$ are the same or different and represent alkyl groups with 1 to 18 carbon atoms, of which one of the $R^6$, $R^7$ and $R^8$ groups can be a $-(CH_2)_3NHCOR^9$ group, in which $R^9$ is an alkyl group with 7 to 17 carbon atoms $X^-$ is any univalent anion and c has a numerical value of 5 to 100.

Thus, we are concerned with di-cationic siloxanes, which in the α, ω positions (terminal) have ammonium salt groups, which are linked through the $R^5$ group to a terminal Si atom of the siloxane.

$R^5$ is a divalent hydrocarbon group. Examples of the $R^5$ group are

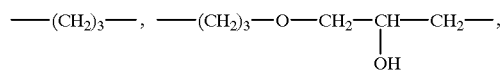
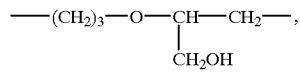
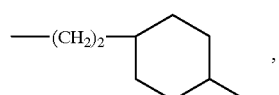
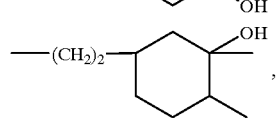
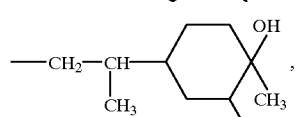
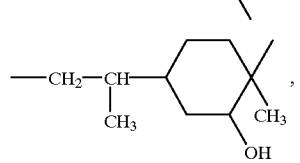

$R^5$ preferably is a group of the formula

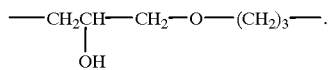

The $R^6$, $R^7$ and $R^8$ groups can be the same or different and are alkyl groups with 1 to 18 carbon atoms; however, one of the aforementioned $R^6$, $R^7$, $R^8$ groups can assume the meaning of the $-(CH_2)_3NHCOR^9$ group.

If the $R^6$, $R^7$, $R^8$ groups represent an alkyl group, they may have 1 to 18 carbon atoms. Particularly preferred are $R^4$ groups, in which two of the aforementioned $R^6$, $R^7$, $R^8$ groups have 1 to 4 carbon atoms and the third group has up to 18 carbon atoms.

If one of the $R^6$, $R^7$, $R^8$ groups is a $-(CH_2)_3NHCOR^9$ group, the $R^9$ group is an alkyl group with 7 to 17 carbon atoms.

$X^-$ is any univalent anion, generally an acetate group. X can, however, also be an inorganic group, such as $Cl^-$.

The subscript "c" gives the number of dimethylsiloxy units in the linear siloxane and has a numerical value of 5 to 100 and preferably of 10 to 80.

Examples of organopolysiloxanes B are

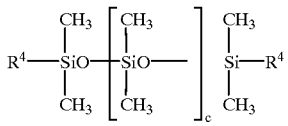

EXAMPLE 1

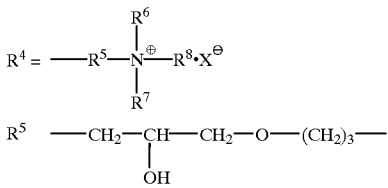

$R^6 = -CH_3$ $R^7 =$ Coconut Fatty Acid $(C_{7-17}CH_3COO^-)$

C=30

EXAMPLE 2

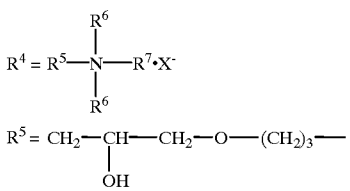

$R^6 = -CH_3$ $R^7 =$ Coconut Fatty Acid $(C_{7-17}CH_3COO^-)$

C=10

The siloxanes A and B are dissolved in water or a water soluble alkylene glycol. Preferably, propylene glycol is used as alkylene glycol.

The inventive medium can optionally contain nonionic surfactants. These nonionic surfactants should be water soluble or water dispersible and therefore usually have an HLB value of 10 to 22. They support and promote the wetting and penetration of the nonwoven material with or through the inventive medium or its aqueous solution. Suitable nonionic surfactants are polyoxyethylene ethers of fatty alcohols, such as products of the addition reaction with 5 to 30 moles of ethylene oxide. The alcohol may contain 6 to 22 carbon atoms, fatty alcohols with 10 to 18 carbon atoms, on the average, being preferred. The polyoxyethylene esters of fatty acids, which are obtainable by the addition reaction of 10 to 50 moles of ethylene oxide with fatty acids having 6 to 22 carbon atoms, can also be used. The fatty alcohols and the fatty acids can have olefinic double bonds. For example, the products of the addition reaction between ethylene oxide and oleyl alcohol or oleic acid, as well as the products of the addition reaction between ethylene oxide and linoleol or linolenic acid are suitable. However, the polyoxyethylene ethers of fatty alcohols are preferred. Products of the addition reaction between ethylene oxide and branched alcohols, such as tridecyl alcohol, are also suitable.

The inventive medium can optionally contain polyalkyl polyether polysiloxane that, in small amounts, can alter the handfeel of the nonwovens treated with the inventive medium. For this purpose, a water dispersible or insoluble organopolysiloxane C, up to 10% by weight, is utilized. Polysiloxane C has the following general formula:

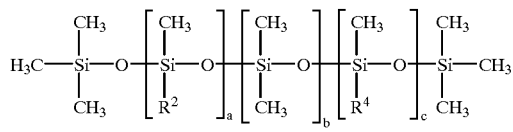

wherein
$R^2$ represents a polyether group $-(C_nH_{2n}O)_xR^3$, wherein $R^3$ is a hydrogen, hydroxyl, alkyl or acyl group and n has a numerical value of 2 to 2.7 and x has numerical value of 2 to 200;
$R^4$ represents an alkyl group $-(CH_2)_yCH_3$ where y is a number from 7 to 21;
a has a number value of 1 to 50;
b has a number value of 1 to 98;
c has a number value of 1 to 25; and
a+b+c is 3 to 150.

Examples of Polysiloxane C are

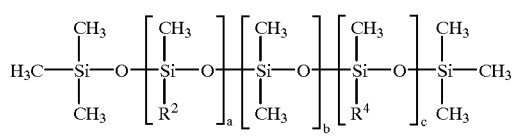

where $R^2$ represents a polyether group $-(C_nH_{2n}O)_xR^3$, and $R^4$ represents an alkyl group $-(CH_2)_yCH_3$

EXAMPLE 1 x=10 n=2.4

$R^3$=CH$_3$ y=15 a=4 b=75 c=21

EXAMPLE 2 x=9 n=2

$R^3$=H y=15 a=4 b=21 c=75

The inventive medium may also optionally contain water insoluble polyalkyl polysiloxane D or dialkoxy polysiloxane polymer E to increase the softness of the treated material. These polymers can be utilized up to 5% by weight each. Polysiloxane D has the following general formula:

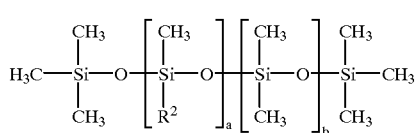

wherein
$R^2$ represents an alkyl group $-(CH_2)_yCH_3$ where y has numerical value of 7 to 21;
a has a number value of 1 to 98;
b has a number value of 0 to 98;
a+b is 1 to 98.

Examples of Polysiloxane D are

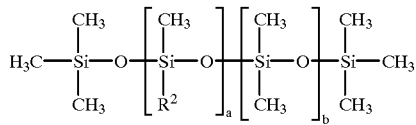

where $R^2$ represents an alkyl group $-(CH_2)_yCH_3$.

EXAMPLE 1 y=17 a=2 b=2

EXAMPLE 2 y=15 a=25 b=75

Polysiloxane E has the following general formula:

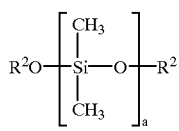

wherein
$R^2$ represents an alkyl group —$(CH_2)_y CH_3$ where y has numerical value of 7 to 21; and
a has a number value of 1 to 98.

Examples of Polysiloxane E are:

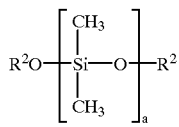

where $R^2$ represents an alkyl group —$(CH_2)_y CH_3$.

EXAMPLE 1 y=21 a=7

EXAMPLE 2 y=15 a=15

Examples of the inventive medium or formulations utilized are listed in the table below. It is understood that these examples are given by way of illustration and not by way of limitation. Some examples of the inventive medium or formulations are as follows:

|  | FORMULA | | | | | | | |
|---|---|---|---|---|---|---|---|---|
| INGREDIENTS | 1 | 2 | 3 | 4 | 5 | 6 | 7 | 8 |
| Organopolysiloxane A | 85 | 80 | 81 | 65 | 77 | 80 | 81 | 75 |
| Organopolysiloxane B | 5 | 10 | 7 | 15 | 4 | 5 | 5 | 10 |
| Propylene Glycol | 10 | 5 | 10 | 20 | 15 | 10 | 8 | 5 |
| Butylene Glycol |  | 5 | — | — | — | — | — | 5 |
| Nonionic Surfactant | — | — | 2 | — | 1 | 3 | 4 | — |
| PA, PE Polysiloxane C | — | — | — | — | 3 | — | — | 5 |
| PA Polysiloxane D | — | — | — | — | — | 2 | — | — |
| DA Polysiloxane E | — | — | — | — | — | — | 2 | — |

PA - Polyalkyl
PE - Polyether
DA - Dialkoxy

The nonwoven materials treated with the inventive medium have a soft, completely pleasant feel. If these products are used as face towels, a non-irritating, thin film of a portion of the inventive medium, which makes the surface of the skin soft or, at least, appear to be soft, remains on the skin.

The syntheses of siloxanes A, B, C, D and E are known from the art. For example, the organopolysiloxanes A can be synthesized by the method in the disclosed European patent application 0 125 779.

The synthesis of the siloxane B with ammonium salt groups is described in U.S. Pat. No. 3,389,160.

The inventive media can be prepared simply by mixing their components by means of a stirrer and, in the event that an aqueous solution is to be used, dissolving them in water. Preferably, the medium is stirred into the required amount of water.

The application properties of the different, inventive media are shown in the following examples. It is understood that these examples are given by way of illustration and not by way of limitation. Formulas referred to below appear in the Table on page 16.

Formula 1
Applied at a rate of 2% solids add-on to a nonwoven base sheet.
Result: The base sheet was softened, water absorbency was not affected. Strength of the fabric was not affected. When the fabric is rubbed against the skin, the skin feels softer.

Formula 4
Applied at a rate of 1.5% solids add-on.
Result: The base sheet is softened, yet feels as though it has more weight, i.e., more loft or thickness. The skin feels conditioned when rubbed with the treated nonwoven. A charge repulsion effect is noticed.

Formula 5
Applied at an add-on of 2.2%.
Result: The nonwoven is softened. No change in fabric dimension. When rubbed against the skin, the skin is not only softened by a slight emolliency, it is also felt on the skin.

Formula 6/7
Applied at levels of 1 to 3%.
Result: Fabric softened, has a heavier, more body feel. Skin is treated to a more emollient afterfeel. The emollient feel is a non-greasy feel.

The wet and dry strength of the nonwoven is not affected by the treatment described above. Typically, water absorption is not changed.

While the invention has been illustrated and described as embodied in nonwovens and a method for softening nonwovens, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. In a combination of a cellulosic nonwoven material and a medium, the improvement wherein the medium comprises:
   45 to 98% by weight of a water soluble or water dispersible polyether polysiloxane A containing ether groups and polysiloxane blocks,
   the polyether groups of which consist of
      30 to 100 mole percent of oxyethylene units,
      the remainder being oxypropylene units, and
   the polysiloxane block of which has 10 to 100 siloxane units;
   1 to 20% by weight of a water soluble or water dispersible organopolysiloxane B with at least one ammonium group linked over a carbon atom; and
   1 to 20% by weight of
      water or
      a water soluble alkylene glycol, provided the ratio of polysiloxanes A:B is between about 12:1 and about 19:1.

2. The combination according to claim 1, wherein the polyether siloxane A is a siloxane of the general, average formula

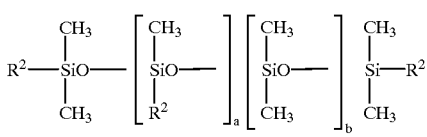

wherein $R^2$ in the molecule is the same or different and represents an alkyl group with 1 to 12 carbon atoms or a polyether group —$(C_nH_{2n}O)_xR^3$, wherein $R^3$ is a hydrogen, alkyl or acyl group and n has a numerical value of 2 to 2.7 and x has a numerical value of 2 to 200, with the proviso that at least one $R^2$ group in the average molecule must be a polyether group;

a has a numerical value of 0 to 98;

b has a numerical value of 0 to 98; and a+b is 8 to 98.

3. The combination according to claim 1, wherein the polysiloxane B contains a siloxane of the general, average formula

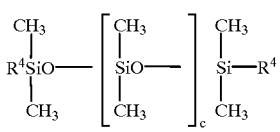

wherein $R^4$ represents the group of the formula

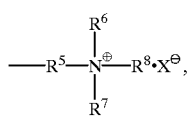

in which $R^5$ is a divalent hydrocarbon group, the carbon chain of which may be interrupted by an oxygen atom, $R^6$, $R^7$, $R^8$ are the same or different and represent alkyl groups with 1 to 18 carbon atoms, of which one of the $R^6$, $R^7$ and $R^8$ groups can be a —$(CH_2)_3NHCOR^9$ group, in which $R^9$ is an alkyl group with 7 to 17 carbon atoms;

$X^-$ is any univalent anion; and c has a numerical value of 5 to 100.

4. The combination according to claim 3, wherein $R^5$ is a group of the formula

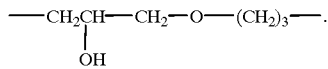

5. The combination according to claim 1, wherein the medium further comprises up to 15% by weight of a water soluble or water dispersible, nonionic surfactant.

6. The combination according to claim 1, wherein the medium further comprises up to 10% by weight of a water dispersible or insoluble organopolysiloxane C.

7. The combination according to claim 6, wherein the polysiloxane C is a siloxane of the general, average formula

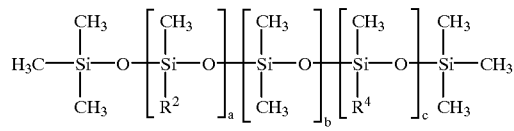

wherein $R^2$ represents a polyether group —$(C_nH_{2n}O)_xR^3$, wherein $R^3$ is a hydrogen, hydroxyl, alkyl or acyl group and n has a numerical value of 2 to 2.7 and x has numerical value of 2 to 200;

$R^4$ represents an alkyl group —$(CH_2)_yCH_3$ where y is a number from 7 to 21;

a has a number value of 1 to 50;

b has a number value of 1 to 98;

c has a number value of 1 to 25; and a+b+c is 3 to 150.

8. The combination according to claim 1, wherein the medium further comprises up to 5% by weight of a water insoluble organopolysiloxane D.

9. The combination according to claim 8, wherein the polysiloxane D is a siloxane of the general, average formula

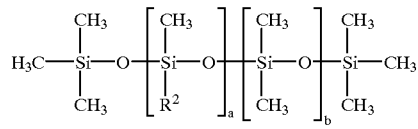

wherein $R^2$ represents an alkyl group —$(CH_2)_yCH_3$ where y has numerical value of 7 to 21;

a has a number value of 1 to 98;

b has a number value of 0 to 98; and a+b is 1 to 98.

10. The combination according to claim 1, wherein the medium further comprises up to 5% by weight of a water insoluble organopolysiloxane E.

11. The combination according to claim 10, wherein the polysiloxane E is a siloxane of the general, average formula

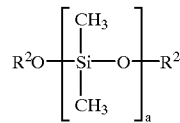

wherein $R^2$ represents an alkyl group —$(CH_2)_yCH_3$ where y has numerical value of 7 to 21; and a has a number value of 1 to 98.

12. The combination according to claim 1, wherein the material is a handkerchief, face towel, toilet paper, or facial tissue.

13. The combination according to claim 1, wherein the medium is dissolved in water to form a 20 to 50% by weight solution.

14. The combination according to claim 1, wherein the alkylene glycol is propylene glycol.

15. The combination according to claim 1, wherein the amount of medium is 0.3 to 5% by weight, based upon the cellulosic nonwoven material.

16. The combination according to claim 15, wherein the medium further comprises up to 10% by weight of a water dispersible or insoluble organopolysiloxane C.

17. The combination according to claim 15, wherein the medium further comprises up to 5% by weight of a water insoluble organopolysiloxane D.

18. The combination according to claim 15, wherein the medium further comprises up to 5% by weight of a water insoluble organopolysiloxane E.

19. The combination according to claim 1, wherein the medium further comprises a water dispersible or insoluble organopolysiloxane C;

a water insoluble organopolysiloxane D; and a water insoluble organopolysiloxane E.

* * * * *